United States Patent [19]
He

[11] Patent Number: 6,107,631
[45] Date of Patent: Aug. 22, 2000

[54] SELF-CALIBRATION APPROACH FOR TUNABLE LASER SPECTRAL ABSORPTION SENSORS

[75] Inventor: Gang He, Morristown, N.J.

[73] Assignee: AlliedSignal Inc., Morristown, N.J.

[21] Appl. No.: 09/041,896

[22] Filed: Mar. 13, 1998

[51] Int. Cl.[7] ................................................. G01N 21/35
[52] U.S. Cl. .............................. 250/339.09; 250/339.13; 250/339.01; 250/339.03
[58] Field of Search ........................ 250/339.09, 339.13, 250/339.01, 339.03

[56] References Cited

U.S. PATENT DOCUMENTS 5,508,525   4/1996   Day et al. ........................... 250/339.09
5,965,887   10/1999  Patton ................................ 250/339.09

*Primary Examiner*—Constantine Hannaher
*Assistant Examiner*—Andrew Israel
*Attorney, Agent, or Firm*—Larry J. Palguta

[57] ABSTRACT

An on-line self-calibrating system where prior calibration information is updated by combining prior stored calibration information with current sensor reading information to simulate the introduction of a known calibrating sample and to generate new calibration information. A preferred embodiment of the present invention is in a laser spectral absorption system for determining the concentration of a particular gas in a gaseous sample by sensing a characteristic narrow spectral pulse in the absorption characteristics of the sample, the area or spectral integration of the pulse being proportional to the concentration of the particular gas. The disclosed technique effects on-line recalibration of the system based on current operating parameters of the system to compensate for time or usage induced degradation in system accuracy without introducing a sample of a known concentration of the gas into the system.

6 Claims, 7 Drawing Sheets

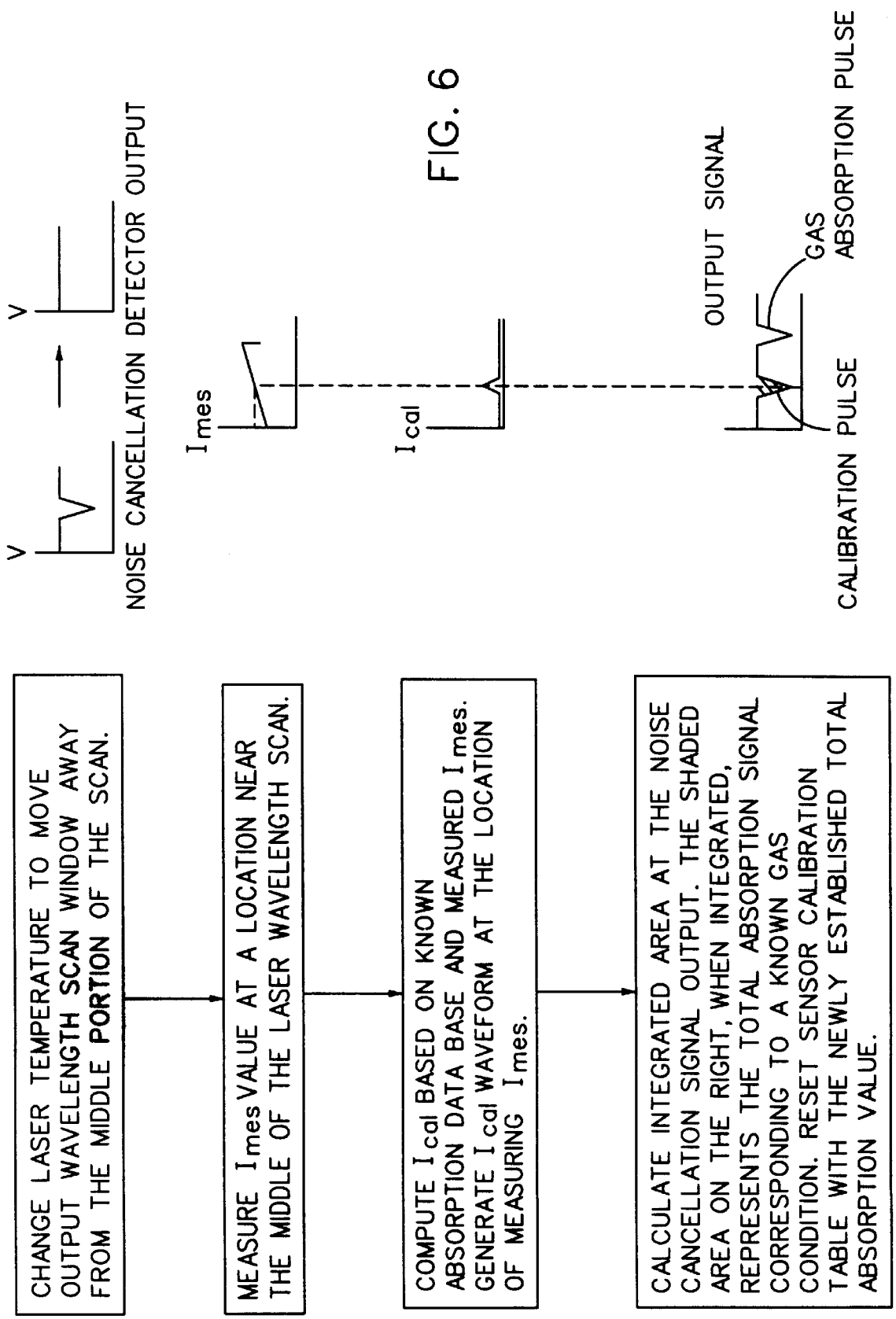

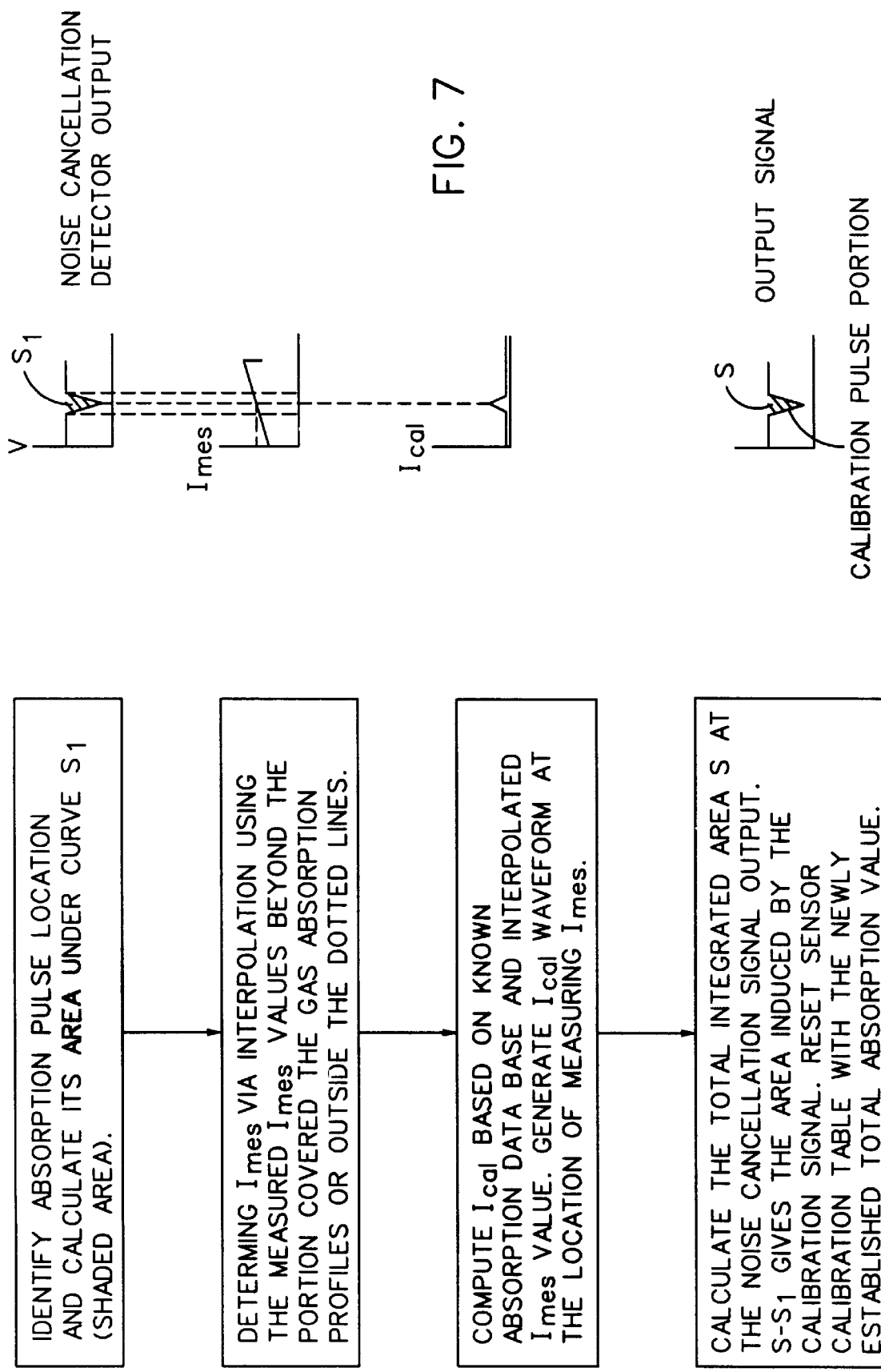

SELF-CALIBRATION APPROACH FOR TUNABLE LASER SPECTRAL ABSORPTION SENSORS

BRIEF SUMMARY OF THE INVENTION

The present invention relates generally to optical measurement methods and apparatus for determining the composition of a mixture of gases, and more especially to such methods and apparatus for achieving on-line recalibration of such optical measurement apparatus. In an illustrative embodiment, the original system calibration table for a ratiometric detector-based diode laser sensor system is selectively updated to compensate for time or usage induced degradation in system accuracy.

In my copending U.S. patent application Ser. No. 08/646,996, incorporated by reference herein, a noise cancellation detection electronic circuit design for laser spectral absorption gas sensors is described. This noise cancellation system balances the photo-currents derived by a measurement signal and a reference signal of a sensor. The invention has application in any measurement device which detects a small signal in combination with high noise content and further utilizes a reference signal. The invention is useful in an optical measurement system by splitting an optical beam into measurement and reference optical beams and passing the measurement beam through a sample cell for measurement information. The measurement beam and reference beam are converted into a measurement current representing information signals impressed on a current signal that is modulated by undesirable noise signals and a reference current representing the carrier current signal exclusive of the information signals and modulated by the noise signals respectively. Then there is generated a voltage source as a function of the reference current and a feedback control voltage resulting in the flow of a correction current modulated by the noise signals. The measurement current and correction current are then combined to substantially cancels the undesirable noise signals from the measurement current and produces a feedback control voltage which comprises an output signal containing the information component of measurement current. Other applications include acoustic, infrared, frequency or other types of measurement systems. Such gas sensors, when used with semiconductor lasers at various wavelengths, are useful in various areas of gas species detection for aerospace and nonaerospace applications. Among the examples are gas sensors for space life-support system applications where gas composition must be monitored and controlled. Similar applications are also abundant in environmental health monitoring and industrial processes control applications.

Optical-based sensor response characteristics may change after initial calibrations due to factors such as component aging, characteristics shift of optical beam splitting components, detector characteristics variations, etc. These are not unique problems for diode laser absorption gas species sensors, but common and sometimes detrimental problems for many optical based sensor systems. In field applications, a laser spectral gas sensor's accuracy may be degraded over time due to various factors. For example, contamination may gradually build up on internal components, or light sources and other optical components characteristics, such as optical transmission, beam splitting ratio, etc. may slowly evolve. These factors in general will not cause a sensor system to fail catastrophically. However, they often affect the system accuracy beyond acceptable levels. The common practice to solve these problems is to perform recalibration by taking the sensor system off-line or to isolate the sensor from the gases to be measured and providing a known amount of gases into the sensor. Such an approach is cumbersome, labor intensive, very costly, and in many cases highly undesirable and impractical. This is even more problematic if the gases to be monitored are toxic or explosive. A reliable mean of self-calibration to ensure sensor system accuracy is highly desirable and useful for many applications.

In order for the ratiometric detector-based diode laser sensor to be successfully implemented in severe environmental condition applications with long calibration span and high reliability requirements, novel self-calibration approaches are required. The self-calibration techniques of the present invention are applicable to a variety of different gas species, having different sensitivity levels. The present invention relates to a new technique that enables such gas sensors to be self-calibrated for long-term in-field applications. There are several advantages to technique. The self-calibration is performed without using any gas handling or introducing any gases. The self-calibration is performed without removing the device from the its original installation. The gas medium to be measured need not to be isolated. The calibration is performed without operator intervention. The calibration is completely software controlled and can be either implemented periodically or on-demand. The present invention will significantly improve sensor accuracy and reliability, and will significantly simplify maintenance and recalibration of these devices, all of which leads to lower operation cost.

The present invention uses an electronic approach to generate absorption features that accurately simulate spectral absorption signals generated by a known concentration of gases in the sensor, when measured under present sensor system conditions. The present sensor operating conditions and its response may be significantly different from the time when the sensor is first calibrated and installed. As such, multiple points of present sensor response to known gas conditions can be obtained to re-establish a current sensor calibration table which allows accurate measurements of unknown gas conditions. This is equivalent to the conventional approach of taking a sensor off-line and injecting known amounts of gases to produce the necessary spectral absorption signals to achieve sensor in-field recalibration. The present invention will eliminate all the complications related to gas handling and operator intervention. Additionally, since semiconductor laser diodes have become highly reliable and consistent over the past decade with typical device life-time on the order of 100,000 to 1,000,000 hours, coupled with reliability and consistency of modern digital and analog electronics devices, this electronic self-calibration approach provides both high reliability and ease-of-use for fieldable sensors.

The present invention comprises, in a spectral absorption system for determining the concentration of a particular gas in a gaseous sample using a sensor to sense a characteristic narrow spectral pulse in the absorption characteristics of the sample the area of which is proportional to the concentration of the particular gas, a method of on-line recalibration of the system to compensate for time or usage induced degradation in system accuracy without introducing a sample of a known concentration of the gas into the system comprising;

storing information relating to prior sensor response and a known gas concentration;

combining a stored sensor response to a particular known gas concentration with a present sensor response to simulate a present sensor response to said particular known gas concentration, in the presence of an imprecisely known concentration of the particular known gas; and updating the stored information to provide information relating the present sensor response and the particular known gas concentration.

BRIEF DESCRIPTION OF THE DRAWINGS

FIG. 6 is a functional block diagram illustrating the self-calibration process in a second mode; and FIG. 7 is a functional block diagram illustrating the self-calibration process in a third mode.

Corresponding reference characters indicate corresponding parts throughout the several views of the drawings.

DESCRIPTION OF THE PREFERRED EMBODIMENT

Figure 1:
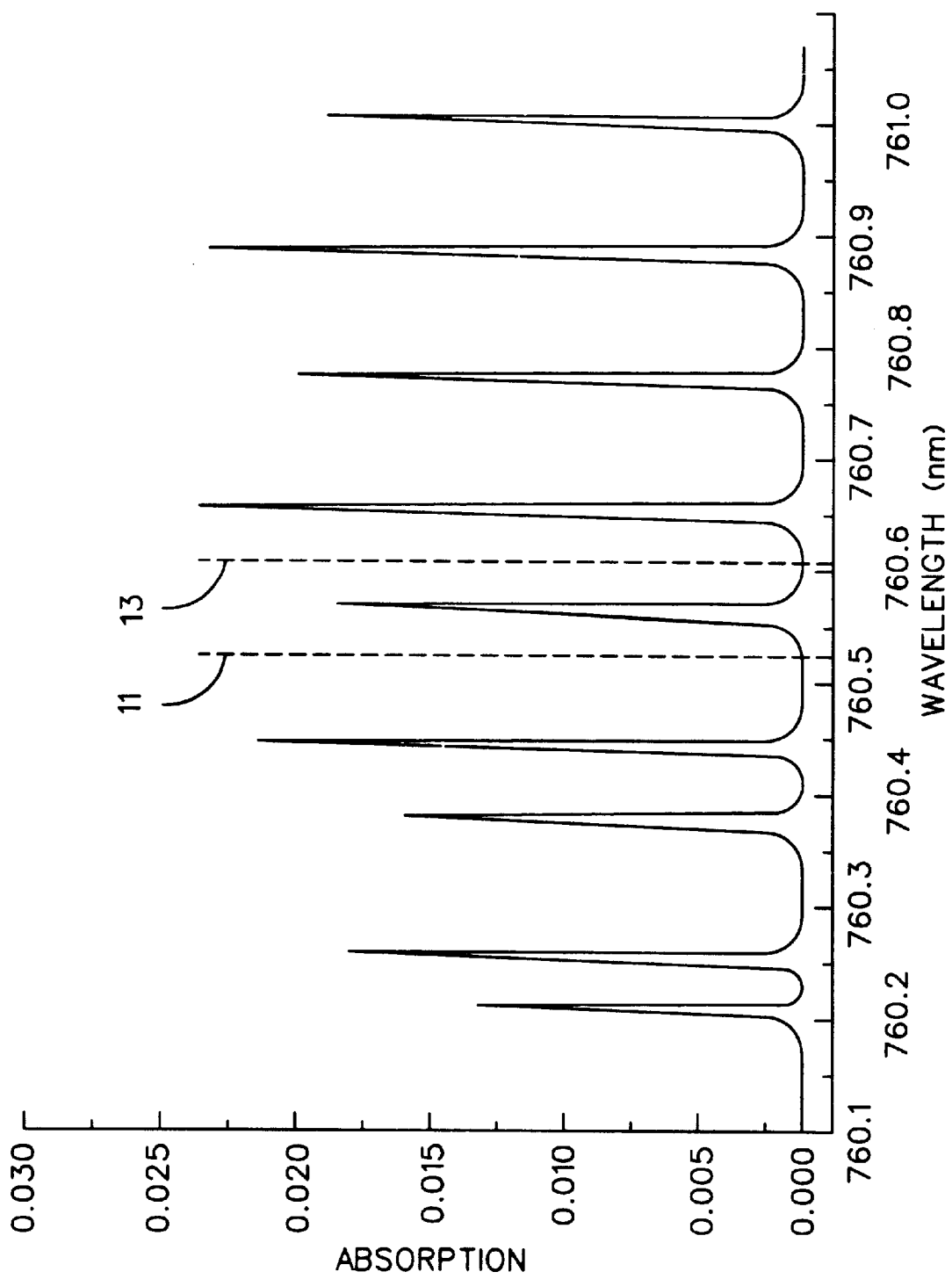
FIG. 1 is a graph of a narrow band of absorption characteristics of oxygen.

Most gas species have unique optical spectral absorption finger-prints. For example, oxygen has a set of spectral absorption lines at the optical wavelengths around 760 nm, while carbon dioxide has one set of absorption lines at around 2.0 $\mu$m. The oxygen absorption lines are shown in FIG. 1. The vertical scale represents the fraction of optical intensity attenuation when a laser beam of certain optical wavelength is passing through room air, and a photo-detector (converting light intensity into current) is placed at a distance of 1 meter away from the laser to measure optical intensity. For example, at the wavelength of 760.57 nm as shown by the peak enclosed by the dotted lines 11 and 13 in FIG. 1, the peak intensity attenuation is about 2%, while the intensity attenuation is zero at 760.52 nm. Therefore, if the output optical wavelength of a laser is tuned across the absorption peak in-between the dotted lines 11 and 13, the output signal at the photo-detector will show a signal drop or notch proportional to the scanned absorption pulse shape. The oxygen concentration, total pressure, and gas temperature determine the absorption line shape, and the total area under the absorption peak is proportional to the oxygen concentration, independent of gaseous medium total pressure and temperature.

Figure 2:
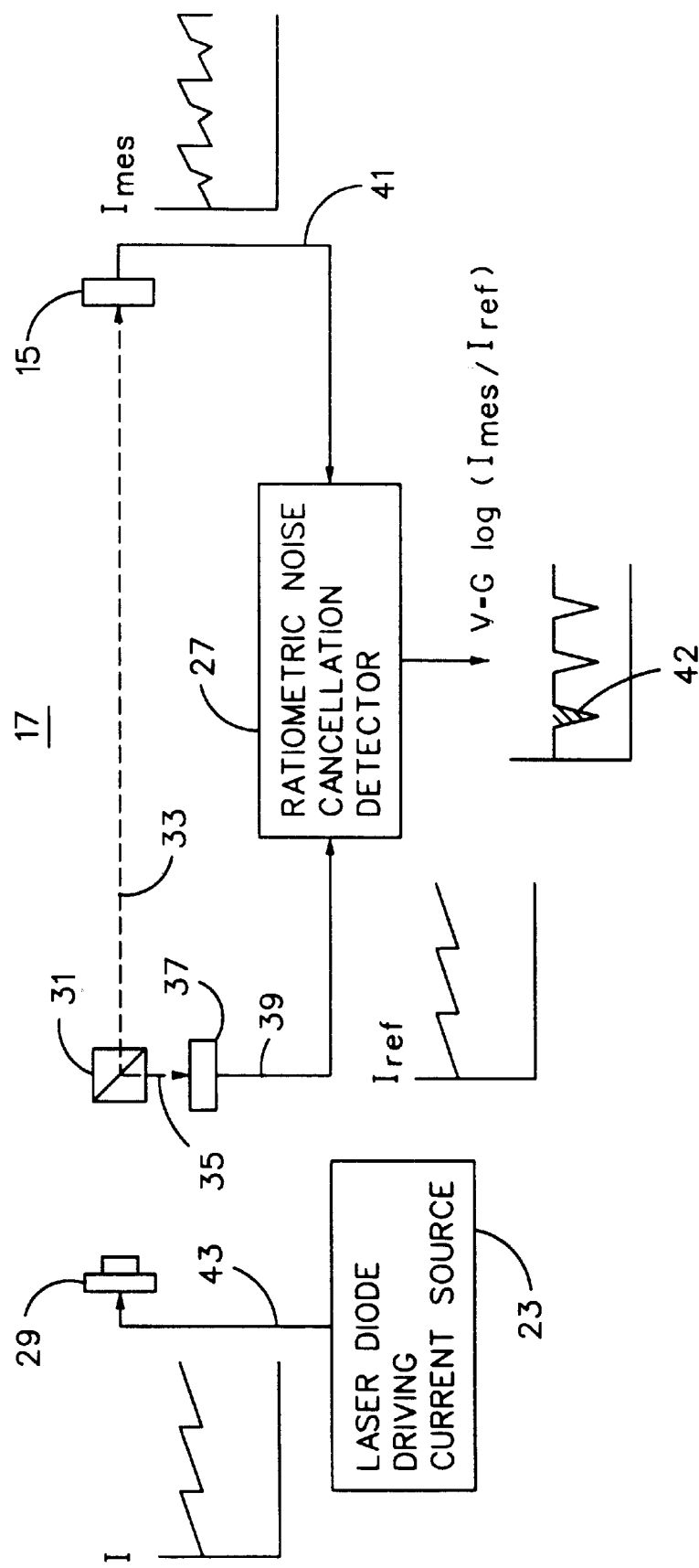
FIG. 2 is a schematic block diagram of spectroscopy apparatus incorporating the noise cancellation feature of my prior copending application.

Output optical wavelength of semiconductor laser diodes can be tuned by changing case operating temperatures and injection current. As such, a tunable diode laser gas sensor can be constructed as shown in FIG. 2, using the noise cancellation detection electronics 23 described in my above mentioned copending patent application. Other types of detection circuits that utilize photo-current for light intensity sensing could also be used. In FIG. 2, a repeating current ramp from current source 23 is applied on line 43 to a laser diode 29 which modulates its output wavelength and intensity, allowing that output to scan a spectral absorption line. The output of laser diode 29 is divided into two beams 33 and 35 by a beam splitter 31. Only beam 33 passes through the gas sample in cavity 17. Both measurement 15 and reference 37 photo detectors convert the respective measured optical intensities into photo currents $I_{mes}$ on line 41 and $I_{ref}$ on line 39 respectively. The gas concentration information to be measured is imbedded in the signal on line 41.

Since the wavelength scanning shown in FIG. 2 covers an entire absorption line, the area enclosed by the absorption peak signal (shaded area 42) is proportional to the gas concentration to be measured. Using Beer's law, a known gas concentration in the gas cavity 17 with a spectral absorption path length L will decrease $I_{mes}$ value to $e^{-\alpha} \cdot I_{mes}$ where $\alpha = N v S L$; wherein v contains wavelength dependent spectral absorption information, such as the shape of the absorption lines shown in FIG. 1 for oxygen. S is the known absorption line strength. N is the gas species number density or the concentration. When integrating over the measured spectral absorption line or calculating the shaded area 42 in FIG. 2, v is normalized to a constant value of 1. Therefore, a known gas concentration (N) inside the sensor gas cavity 17 in FIG. 2 generates an absorption line shape signal with well defined parameters such as total area under curve. After the sensor is calibrated against this known gas condition, subsequently measurements of unknown gas conditions are compared with this integrated area value to determine the measured gas concentration by a linear relation.

As noted earlier, after such a calibrated sensor is placed in field use for an extended period of time various parameters, such as temperature, humidity and dirt, may lead to the original system calibration to change, shifting system response characteristics away from that given by the initial calibration table. Readout errors will result due to these unknown changes. The prior approach to updating the calibration table has been to take the sensor off-line, place a known sample in the cavity 17 and update the table entries (conveniently the value of $\alpha$ or of $e^{-\alpha}$) based on the current sensor output and known sample content. The present invention accomplishes a similar updating of the table by a momentary sampling interruption while the cavity operation is unchanged, that is, a sample from the working environment which is of not precisely known components remains in the cavity 17.

Figure 3:
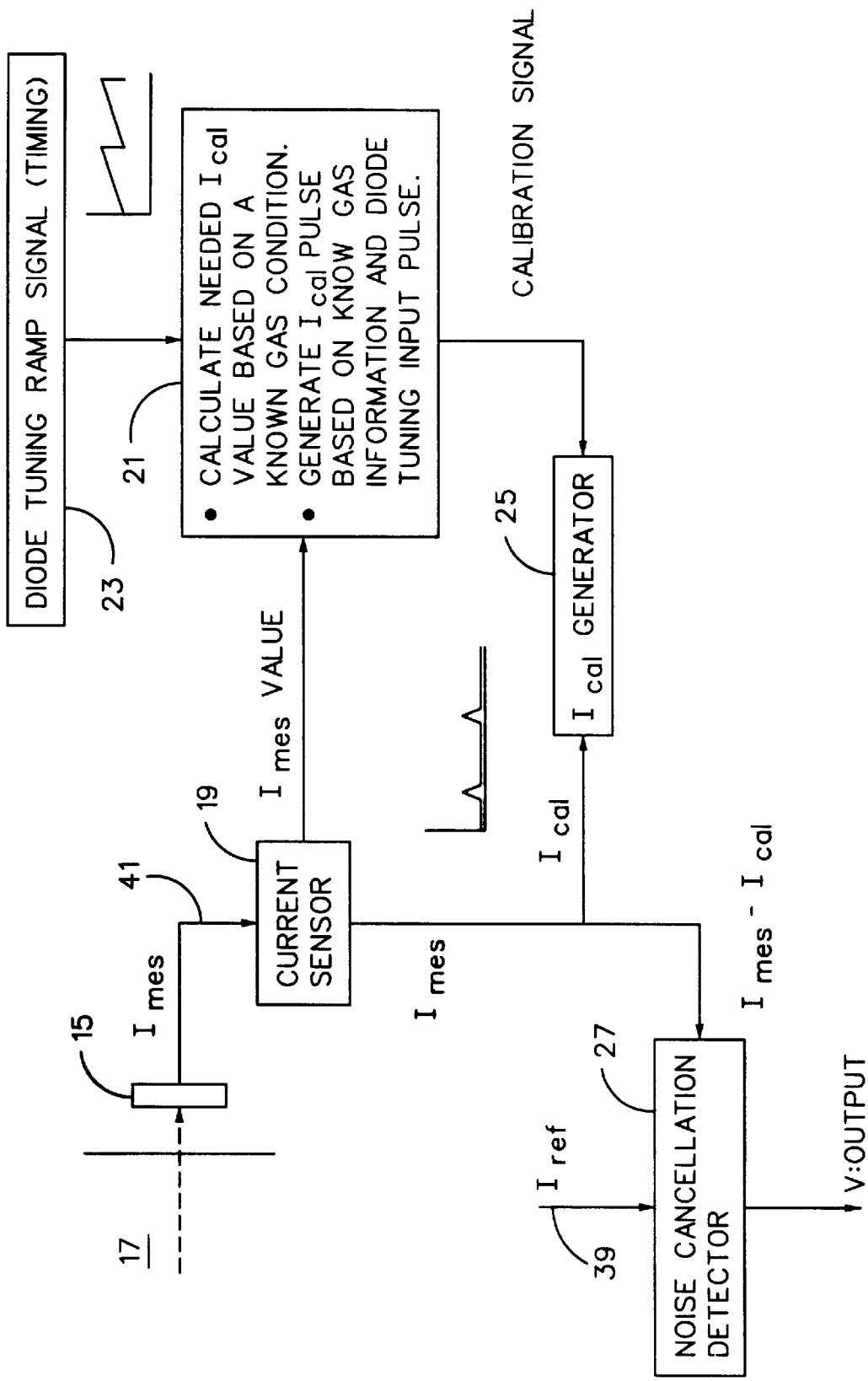
FIG. 3 is a block diagram of the right hand portion of FIG. 2 showing my on-line calibration circuitry.

A photo-current measurement mechanism 19 is added between measurement photo detector 15 and the ratiometric noise cancellation detection electronics 27 as shown in FIG. 3. Such a current measurement mechanism leads to negligible change in the current $I_{mes}$ on line 41. The measured current information is then sent to a signal processing unit 21 that calculates a simulated current reduction value $(1-e^{-\alpha}) \cdot I_{mes}$ based on a previously determined gas attenuation condition ($\alpha$) and the presently measured current $I_{mes}$. A current reduction pulse signal which is timed with the diode laser tuning ramp signal from 23 is generated such that the resultant current reduction signal is positioned somewhat in the middle of the laser diode tuning ramp, as a normal gas absorption line shape signal would be. The generated pulse signal is then sent from 21 to an electronic circuit block 25 that is connected to the measured current path before the noise cancellation detector electronics. The pulse signal causes a current diversion of $I_{cal} = (1-e^{-\alpha}) \cdot I_{mes}$ from the signal path which is equivalent to a known spectral absorption induced current reduction.

Figure 4:
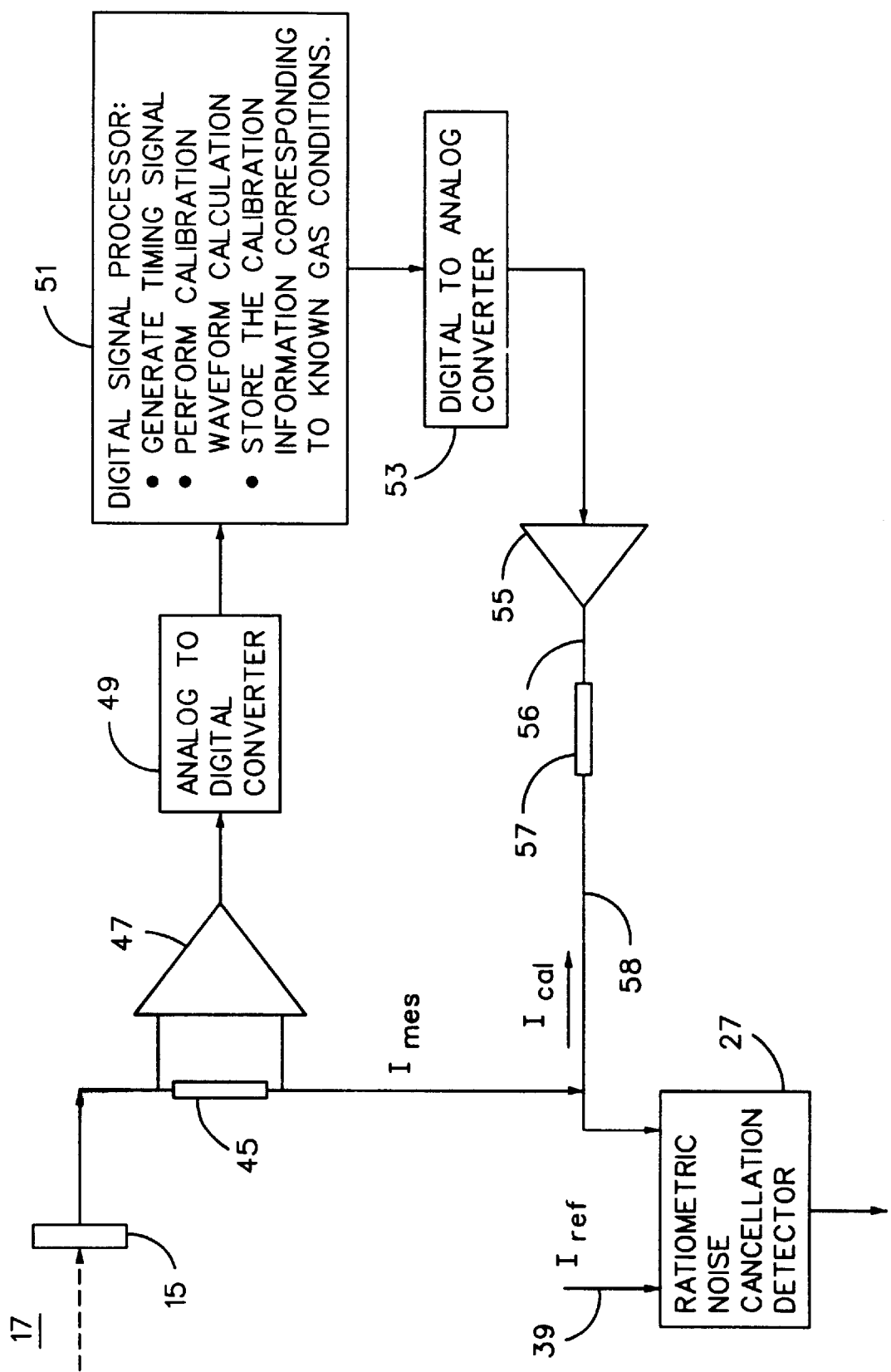
FIG. 4 is a more detailed block diagram showing one implementation of an all electronic self-calibration circuitry.

In FIG. 4, the resistor 45 and the high-input impedance differential operational amplifier 47 form the current sensor 19 of FIG. 3. Since the input impedance of the amplifier 49 is significantly larger than the resistance of resistor 45, the effect on $I_{mes}$ is negligible. The amplifier 47 output is converted to a digital form at 49 and a digital signal processor 51 is used to perform computations, among other functions, such as generating diode tuning ramp signals, that determines the value and timing of calibration current flow based on the previously determined gas conditions and present Imes values. The resistor 57 and the buffer amplifier 55 are used as the calibration current signal generator 25 of FIG. 3. A lower voltage value at node 56 in comparison to node 58 causes an $I_{cal}$ flow. If the ratiometric detector described in my copending U.S. patent application Ser. No. 08/646,996 is used, the voltage value at node 58 is zero. A negative voltage at node 56 will lead to an $I_{cal}$ flow.

Several self-calibration modes can be used to perform the self-calibration. Note that such calibration will be performed while the sensor is on-line. There is no need to isolate the gas medium to be measured.

Figure 5:
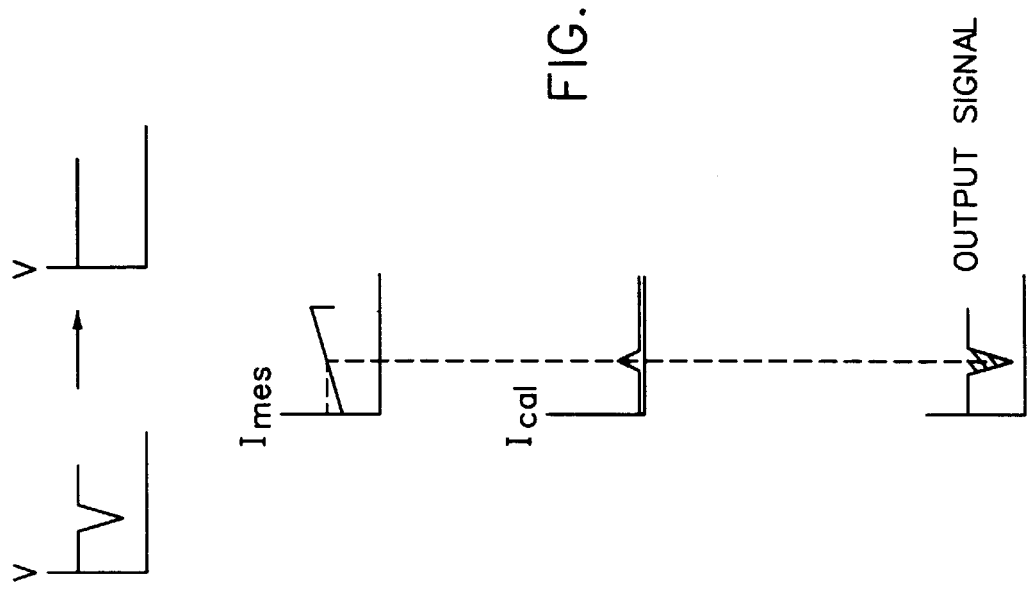
FIG. 5 is a functional block diagram illustrating the self-calibration process in one mode.
Figure 5:
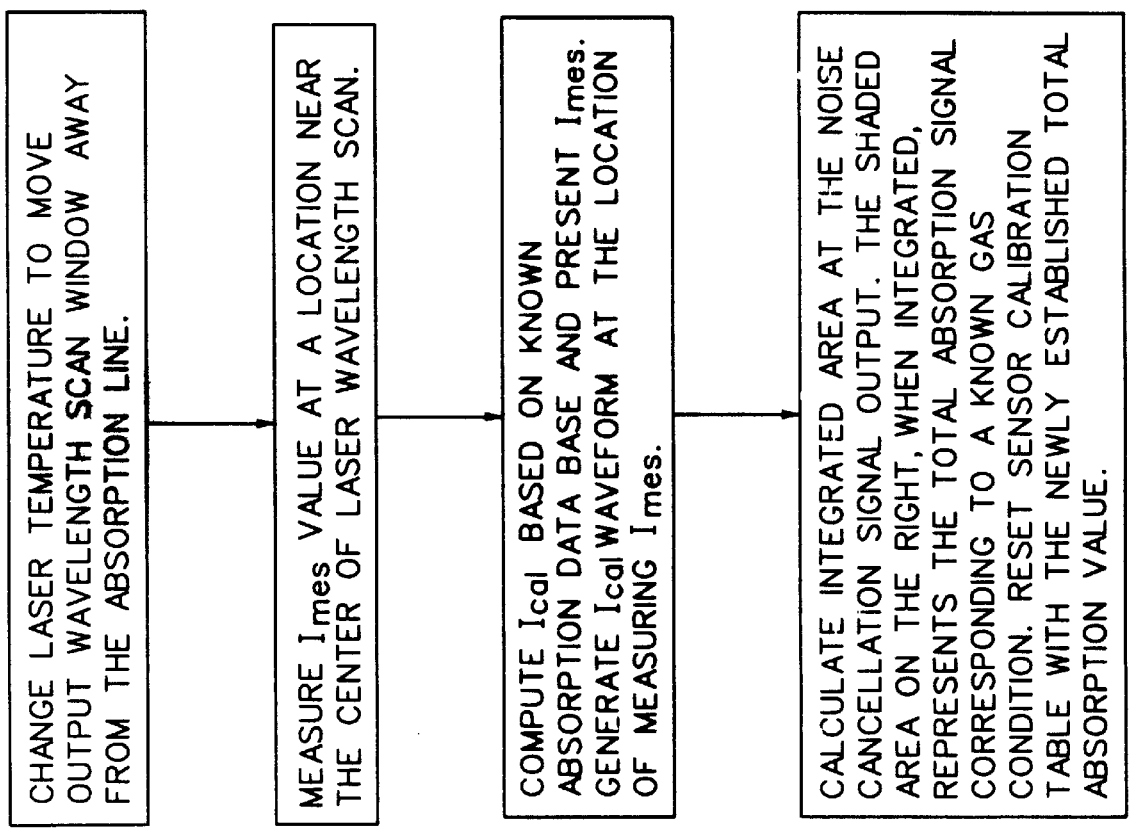

In a first mode as outlined in FIG. 5, the laser output wavelength is shifted by, for example, changing the case operating temperature. As such, the spectral scanning window, as shown by the wavelength range enclosed by dotted lines 11 and 13 in FIG. 1, is shifted to an adjacent location next to the spectral absorption line without enclosing the absorption line. The spectral scan will not produce a gas absorption line shape signal. $I_{mes}$ is then measured and the computation is performed to calculate the corresponding $I_{cal}$ value based on the pre-determined gas absorption condition ($\alpha$). A voltage waveform that causes $I_{cal}$ flow is then generated. This mode is best suited to situations where the separation between spectral lines is well defined as shown in FIG. 1 and when the diode is easily tuned over the required range.

In a second mode as depicted in FIG. 6, the diode output wavelength is shifted by changing the operating temperature or DC driving current. Here, the spectral scanning window covers the part or whole spectral absorption line. However, there is sufficient space left to position the calibration pulse. This mode is best suited to situations where the laser diode may have a limited tuning range or sufficient tuning is not available for other reasons.

In yet a third mode as shown in FIG. 7, the diode output wavelength is not shifted and the spectral scanning window covers the spectral absorption line of interest. Here, the process of obtaining $I_{mes}$ requires interpolation. This mode is best suited to situations where tuning of the diode output and its associated scanning window may lead to interference from certain adjacent spectral absorption lines coming from the gas sample to be measured or from different gas species.

What is claimed is:

1. In a spectral absorption system for determining the concentration of a particular gas in a gaseous sample using a sensor to sense a characteristic narrow spectral pulse in the absorption characteristics of the sample the area of which is proportional to the concentration of the particular gas, a method of on-line recalibration of the system to compensate for time or usage induced degradation in system accuracy without introducing a sample of a known concentration of the gas into the system comprising;

storing information relating to a prior sensor response and a known gas concentration;

combining a stored sensor response to a particular known gas concentration with a present sensor response to simulate a present sensor response to said known particular gas concentration, in the presence of an imprecisely known concentration of the particular known gas; and updating the stored information to provide information relating the present sensor response and the particular known gas concentration.

2. The method of claim 1, wherein the step of combining includes removing characteristic narrow spectral pulse information from the present sensor response, generating a narrow pulse indicative of the sensor response to the particular known gas concentration, and superimposing the generated narrow pulse on the present sensor response where the characteristic narrow spectral pulse information was removed to create a simulated present sensor response.

3. The method of claim 1, wherein the spectral absorption system includes at least one photo-sensitive cell for providing an output current $I_{mes}$ which includes characteristic narrow spectral pulse information, the method further comprising the steps of sampling a current $I_{mes}$, retrieving a value $\alpha$ from the stored information, combining the retrieved value of $\alpha$ and the sampled current $I_{mes}$ to create a simulated current reduction value $I_{cal}=(1-e^{-\alpha}) \cdot I_{mes}$, subtractively combining $I_{cal}$ and $I_{mes}$ to simulate a current indicative of a present sensor response to the known concentration of said gas, wherein $\alpha$ represents wavelength dependent spectral absorption information, and e is a constant.

4. The method of claim 3, wherein the step of updating includes replacing the prior sensor response by the present sensor response which is determined by the simulated current reduction value.

5. The method of claim 3, wherein the spectral absorption system includes a tunable laser diode source with the imprecisely known concentration of the particular gas located intermediate said source and said sensor, the method further including energizing the laser diode with a current ramp to provide an output therefrom which varies both in wavelength and magnitude, and the step of combining including utilizing the current ramp to delete the characteristic narrow spectral pulse information from $I_{mes}$.

6. The method of claim 3, wherein the spectral absorption system includes a laser diode source with the imprecisely known concentration of the particular gas located intermediate said source and said sensor, and the step of combining includes changing at least one of the temperature and DC bias current of a laser diode to shift the wavelength of an output thereof thereby deleting the characteristic narrow spectral pulse information from $I_{mes}$.

* * * * *